United States Patent
Cheng

(10) Patent No.: US 6,355,071 B1
(45) Date of Patent: Mar. 12, 2002

(54) KNEE JOINT CAPABLE OF ROTATING RAPIDLY IN ONE DIRECTION BUT SLOWLY IN THE OTHER

(75) Inventor: Chia Pao Cheng, Taipei (TW)

(73) Assignee: Ken Dali Enterprise Co., Ltd., Taipei Hsien (TW)

( * ) Notice: Subject to any disclaimer, the term of this patent is extended or adjusted under 35 U.S.C. 154(b) by 0 days.

(21) Appl. No.: 09/459,488

(22) Filed: Dec. 13, 1999

(51) Int. Cl.⁷ .................................................. A61F 2/64

(52) U.S. Cl. ......................................................... 623/45

(58) Field of Search ............................... 623/39, 43–46, 623/38

(56) References Cited

FOREIGN PATENT DOCUMENTS

DE      39 23 056 A  *  1/1991  .................. 623/43

\* cited by examiner

*Primary Examiner*—David H. Willse
(74) *Attorney, Agent, or Firm*—A & J

(57) ABSTRACT

A knee joint utilizes a shaft to dispose a rotating portion inside a body portion thereby enabling the body portion to rotate with respect to the shaft, the rotating portion being provided with a one-way bearing which enables the rotating portion to return rapidly to original position thereof in counterclockwise direction and utilizes a cushioning device and larger friction to cause the rotating portion to bend slowly in clockwise direction, thereby enabling people with disability to control and operate artificial limbs conveniently and easily.

1 Claim, 4 Drawing Sheets

KNEE JOINT CAPABLE OF ROTATING RAPIDLY IN ONE DIRECTION BUT SLOWLY IN THE OTHER

BACKGROUND OF THE INVENTION

1. Field of the Invention

This invention is related to a knee joint and in particular to one which can be rotated rapidly in one direction but slowly in the other.

2. Description of the Prior Art

It has been found that people with leg disabilities in society recently have been using artificial limbs to move, in order to facilitate their movements, thus enabling them to walk as if they have feet. Hence, various kinds of knee-joint structures for simulating the movement of the knee joint have been developed to meet the above-mentioned needs. However, the artificial limbs are mechanical structures, and require people with leg disabilities to move the thigh part of the leg in order to operate the artificial limb(s). The commonly used artificial limb includes an urging device which utilizes an axle to make it rotate with respect to a shaft. However, as the artificial limbs are not the real portion of a person's body, they are difficult to control and move smoothly. The artificial limbs are rotated too quickly when they are rotated in a walking movement. If the artificial limbs are turned excessively they will not be able to pass the urging sleeve, thereby making the artificial limbs move rapidly into a right angle. This creates a lack of support so that people with disabilities will fall down and injure themselves. Once the artificial limbs are bent at an angle, they cannot return to their original positions quickly, so that people with disabilities can only walk using small steps. Consequently, such conventional artificial leg joints are inconvenient and unsafe to use.

Therefore, it is an object of the present invention to provide an improvement in the structure of a knee joint which can obviate and mitigate the above-mentioned drawbacks.

SUMMARY OF THE INVENTION

This invention is related to an improvement in the structure of a knee joint.

According to preferred embodiment of the present invention, a knee joint utilizes a shaft to dispose a rotating portion inside a body portion thereby enabling the body portion to rotate with respect to the shaft, the rotating portion being provided with a one-way bearing which enables the rotating portion to return rapidly to original position thereof in counterclockwise direction and utilizes a cushioning device and larger friction to cause the rotating portion to bend slowly in clockwise direction, thereby enabling people with disability to control and operate artificial limbs conveniently and easily.

It is the primary object of the present invention to provide an improvement in the structure of a knee joint which can be rotated rapidly in one direction but slowly in the other direction.

It is another object of the present invention to provide an improvement in the structure of a knee joint which can be easily controlled to stop the rotation motion.

It is still another object of the present invention to provide an improvement in the structure of a knee joint which is simple in construction.

It is still another object of the present invention to provide an improvement in the structure of a knee joint which is safe in use.

It is a further object of the present invention to provide an improvement in the structure of a knee joint which can protect the user from injury.

The foregoing objects and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts. Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENT

Figure 1:
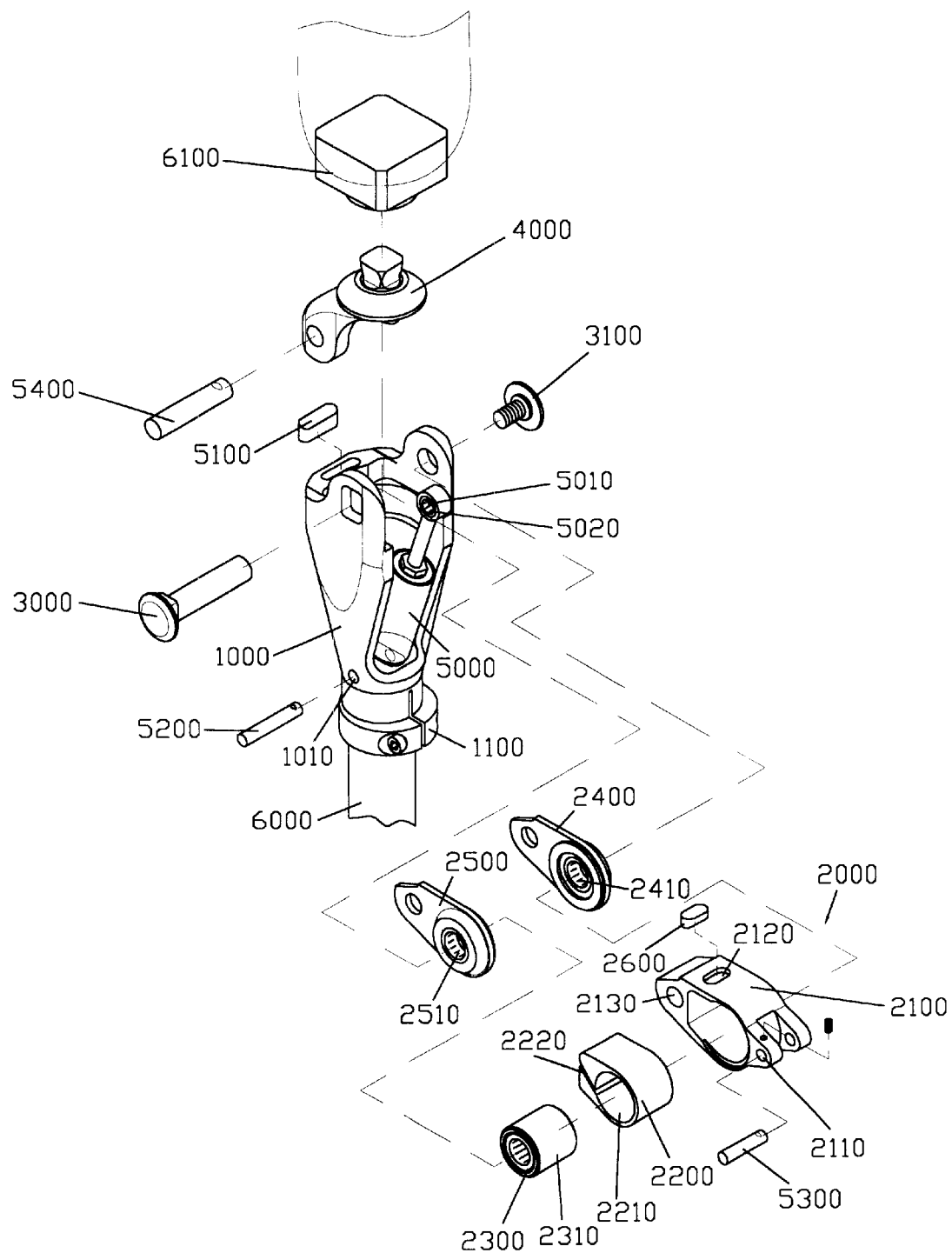
FIG. 1 is an exploded view of the present invention.

For the purpose of promoting an understanding of the principles of the invention, reference will now be made to the embodiment illustrated in the drawings. Specific language will be used to describe same. It will, nevertheless, be understood that no limitation of the scope of the invention is thereby intended, such alterations and further modifications in the illustrated device, and such further applications of the principles of the invention as illustrated herein being contemplated as would normally occur to one skilled in the art to which the invention relates.

With reference to the drawings and in particular to FIG. 1 thereof, the knee joint according to the present invention basically utilizes a shaft 3000 to hold a rotating portion 2000 inside a body portion 1000, so that the rotating portion 2000 can be turned with respect to the shaft 3000. A sleeve 1100 is provided at the lower end of the body portion 1000 for holding a rod 6000 which is to be pivotally connected with ankle and sole. A cushioning device 5000 is pivotally connected with the body portion 1000 by a pin 5200 extending through a hole 1010 at the lower end of the body portion 1000, so that the cushioning device 5000 can be rotated with respect to the pin 5200. The other end of the cushioning device 5000 is rotatably connected with a rear end of the rotating body 2100 by a pin 5300 which extends through the holes 2110 of the rotating device 2100 and a hole 5010 of the cushioning device 5000, so that when the rotating device 2100 is turned in clockwise direction (see FIG. 3), the cushioning device 5000 will slow the motion of the rotating device 2100 thereby preventing the user from unequilibrium and therefore keeping the user from danger. Further, an elastomer 5100 is fitted on the top of the body portion 1000 for absorbing the shock and impact produced when the rotating portion 2000 is returned.

A pivot portion 6100 is installed in the thigh of a user and a cover 4000 is engaged with the pivot portion 6100. The cover 4000 is connected with the rotating device 2100 by a pin 5400 extending through a hole 2130 of the rotating device 2100.

Figure 2:
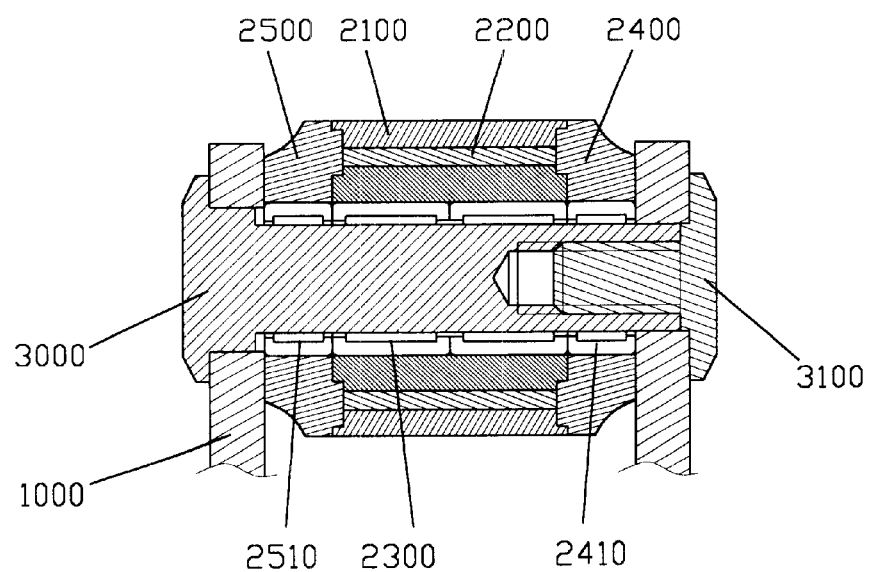
FIG. 2 is a longitudinal sectional view of the present invention.

Referring to FIG. 2, a sleeve 2200 and a one-way bearing 2300 are fitted in the rotating device 2100 of the rotating portion 2000, and two baffles 2400 and 2500 are mounted on two ends of the rotating device 2100. The shaft 3000 extends through the body portion 1000 and the rotating device 2100 to engage with a screw 3100 so that the rotating device 2100 can be rotated with respect to the shaft 3000. The baffles 2400 and 2500 are provided with bearings 2410 and 2510, respectively, so as to smooth the rotation of the rotating portion 2000. In addition, the upper of the cushioning device 5000 is provided with a bearing 5020 for smoothing the rotation of the cushioning device 5000.

Figure 3:
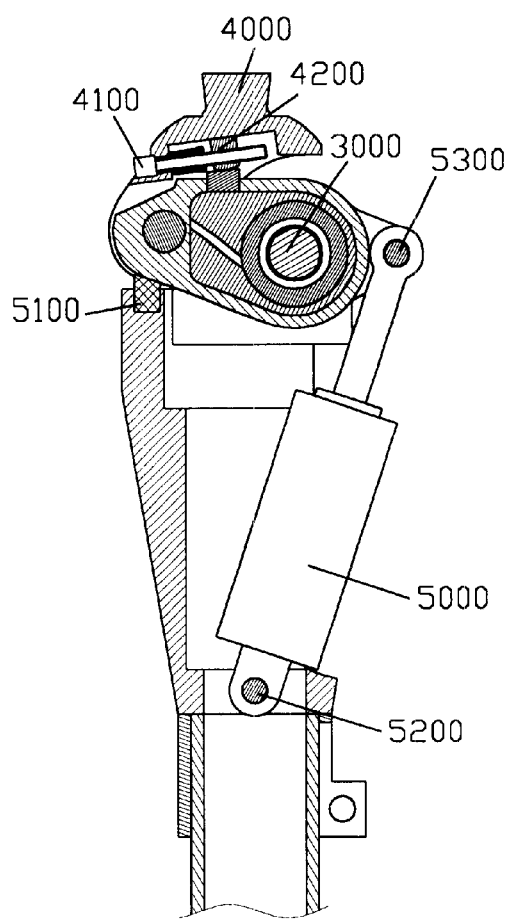
FIGS. 3 and 4 illustrate the working principle of the present invention.
Figure 4:
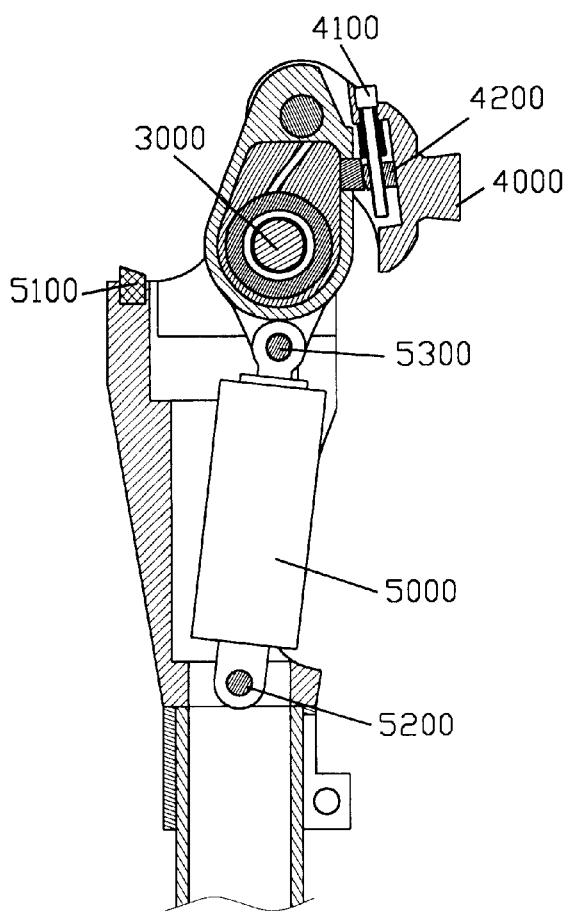

Referring to FIGS. 3 and 4, when the cover 4000 is turned with respect to the shaft 3000 to a position where the cushioning device 5000 cannot retract any more, the cushioning device 5000 can still decrease the rotation speed. Within the cover 4000 there is a screw 4100 which is engaged with a press rod 4200 so that the turning of the screw 4100 can adjust the position of the press rod 4200. By means of the adjustment of the position of the press rod 4200, the applied force can be adjusted.

Figure 5:
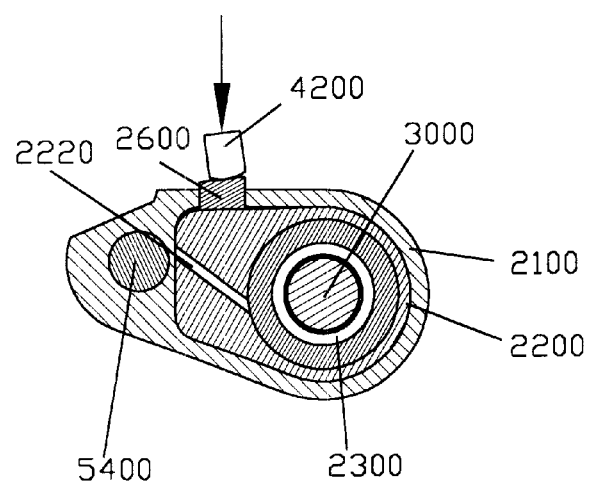
FIG. 5 illustrates how to depress the button to stop the rotation motion.
Figure 6:
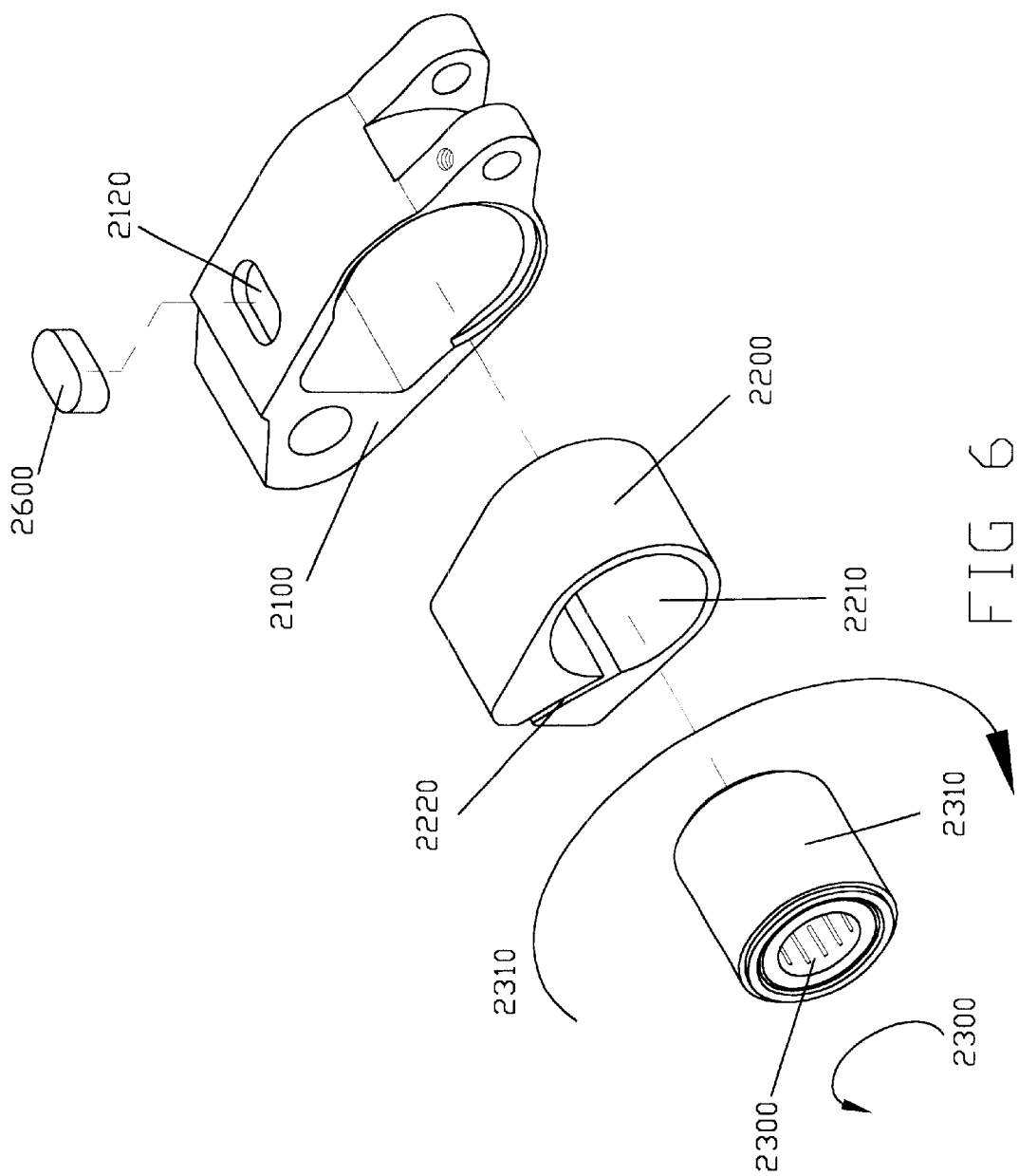
FIG. 6 is an exploded view of the rotating device.

As shown in FIGS. 5 and 6, the one-way bearing 2300 only rotates in one direction only so that only when the rotating portion 2000 is rotated counterclockwise will the bearing 2300 rotate. When the rotating portion 2000 is turned clockwise, the one-way bearing 2300 cannot be rotated so that the outer surface 2310 of the one-way bearing 2300 will be rotated in unison with the rotating portion 2000. As the outer surface 2310 of the one-way bearing 2300 is rotated inside the sleeve 2200, the friction therebetween will be increased thus causing the rotating portion 2000 to rotate rapidly in counterclockwise direction but rotate slowly in clockwise direction. In addition, the rotating device 2100 is formed with an orifice 2120 on the top in which is fitted a button 2600. As the button 2600 is depressed, the clearance 2220 of the sleeve 2200 will be decreased thereby increasing the friction between the outer surface 2310 of the bearing 2300 and the inner surface 2210 of the sleeve 2200 thereby braking the rotation motion. Hence, it is only necessary to apply a small amount of force to stop the motion. Except in the position where it is impossible to depress the button 2600, the user can stop the rotation motion even if the angle exceeds an angle of 30 degrees.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A knee joint comprising:

a body portion;

a sleeve provided at a lower end of said body portion for holding a rod;

a cushioning device having an end pivotally connected with said body portion via a first pin extending through a hole at said lower end of said body portion, another end of said cushioning device being provided with a bearing;

a rotating device rotatably connected with said bearing of said cushioning device by a second pin which extends through said rotating device, said rotating device having a top formed with an orifice in which is fitted a button;

an elastomer fitted on a top of said body portion for absorbing shock and impact produced;

a pivot portion adapted to be installed in a thigh of a user;

a cover engaged with a bottom of said pivot portion and connected with said rotating device by a third pin extending through said rotating device;

a sleeve member fitted in said rotating device and having a clearance;

a one-way bearing fitted in said sleeve member;

two baffles mounted on two ends of said rotating device and each provided with a bearing;

a shaft extending through said body portion and said one-way bearing to engage with a first screw thereby enabling said rotating device to rotate with respect to said shaft; and a second screw fitted within said cover and engaged with a press rod such that turning of said second screw will adjust position of said press rod.

\* \* \* \* \*